United States Patent
Peters et al.

(10) Patent No.: US 11,827,593 B2
(45) Date of Patent: Nov. 28, 2023

(54) PRODUCTION OF ALKYLAROMATIC COMPOUNDS

(71) Applicant: ExxonMobil Chemical Patents Inc., Baytown, TX (US)

(72) Inventors: Aaron W. Peters, New Hope, PA (US); William J. Knaeble, Bridgewater, NJ (US); Allen W. Burton, Stewartsville, NJ (US); Ivy D. Johnson, Lawrenceville, NJ (US); Christopher G. Oliveri, Bridgewater, NJ (US); Reuben Britto, Redwood City, CA (US)

(73) Assignee: ExxonMobil Chemicals Patents Inc., Baytown, TX (US)

( * ) Notice: Subject to any disclaimer, the term of this patent is extended or adjusted under 35 U.S.C. 154(b) by 0 days.

(21) Appl. No.: 17/764,424

(22) PCT Filed: Sep. 16, 2020

(86) PCT No.: PCT/US2020/051086
§ 371 (c)(1),
(2) Date: Mar. 28, 2022

(87) PCT Pub. No.: WO2021/076260
PCT Pub. Date: Apr. 22, 2021

(65) Prior Publication Data
US 2022/0356132 A1 Nov. 10, 2022

Related U.S. Application Data

(60) Provisional application No. 62/916,427, filed on Oct. 17, 2019.

(30) Foreign Application Priority Data

Jan. 30, 2020 (EP) .................................... 20154687

(51) Int. Cl.
*C07C 6/12* (2006.01)
*B01J 29/70* (2006.01)

(52) U.S. Cl.
CPC ............ *C07C 6/126* (2013.01); *B01J 29/7038* (2013.01)

(58) Field of Classification Search
CPC ......... C07C 2/66; C07C 15/085; C07C 6/126; C07C 2529/70; B01J 29/7038
See application file for complete search history.

(56) References Cited

U.S. PATENT DOCUMENTS 3,293,192 A 12/1966 Maher et al.
3,308,069 A 3/1967 Wadlinger et al.
(Continued)

FOREIGN PATENT DOCUMENTS

EP 0293032 A2 11/1988
WO 97/17290 A1 5/1997
(Continued)

OTHER PUBLICATIONS

Martinez-Triguero, J. et al., (1999) "The Catalytic Performance of 14-Membered Ring Zeolites", Journal of Catalysis, vol. 182, No. 2, pp. 463-469.

*Primary Examiner* — Sharon Pregler

(57) ABSTRACT

A process for producing a monoalkylated benzene comprises contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the catalyst composition comprises a metallosilicate zeolite comprising openings defined by 14-membered rings of tetrahedrally coordinated atoms and the transalkylation conditions include a temperature in the range of 160° C. to 220° C.

21 Claims, 4 Drawing Sheets

(56) References Cited

U.S. PATENT DOCUMENTS

| | | |
|---|---|---|
| 3,415,736 A | 12/1968 | Julius |
| 3,442,795 A | 5/1969 | Kerr et al. |
| 3,449,070 A | 6/1969 | Mcdaniel et al. |
| 3,702,886 A | 11/1972 | Argauer et al. |
| 3,709,979 A | 1/1973 | Chu |
| 3,766,093 A | 10/1973 | Chu |
| 3,832,449 A | 8/1974 | Rosinski et al. |
| 3,894,104 A | 7/1975 | Chang et al. |
| 3,923,636 A | 12/1975 | Mead et al. |
| 3,950,496 A | 4/1976 | Ciric |
| 3,972,983 A | 8/1976 | Ciric |
| 4,016,245 A | 4/1977 | Plank et al. |
| 4,021,947 A | 5/1977 | Shneider |
| 4,076,842 A | 2/1978 | Plank et al. |
| 4,234,231 A | 11/1980 | Yan |
| 4,401,556 A | 8/1983 | Bezman et al. |
| 4,439,409 A | 3/1984 | Puppe et al. |
| 4,556,477 A | 12/1985 | Dwyer |
| 4,826,667 A | 5/1989 | Zones et al. |
| 4,954,325 A | 9/1990 | Rubin et al. |
| 5,098,684 A | 3/1992 | Kresge et al. |
| 5,102,643 A | 4/1992 | Kresge et al. |
| 5,198,203 A | 3/1993 | Kresge et al. |
| 5,236,575 A | 8/1993 | Bennett et al. |
| 5,250,277 A | 10/1993 | Kresge et al. |
| 5,362,697 A | 11/1994 | Fung et al. |
| 6,077,498 A | 6/2000 | Diaz et al. |
| 6,103,215 A * | 8/2000 | Zones .................. C01B 39/48 423/713 |
| 6,756,030 B1 | 6/2004 | Rohde et al. |
| 6,936,744 B1 * | 8/2005 | Cheng .................. C07C 6/126 585/475 |
| 7,527,782 B2 | 5/2009 | Corma et al. |
| 7,713,513 B2 | 5/2010 | Jan et al. |
| 2006/0110321 A1 | 5/2006 | Corma et al. |
| 2012/0088937 A1 | 4/2012 | Jan et al. |
| 2013/0183231 A1 | 7/2013 | Senderov et al. |
| 2013/0197287 A1 * | 8/2013 | Vincent .................. C07C 7/12 585/323 |

FOREIGN PATENT DOCUMENTS

| | | |
|---|---|---|
| WO | 97/46486 A2 | 12/1997 |
| WO | 2018/140149 A1 | 8/2018 |
| WO | 2021/076260 A1 | 4/2021 |

* cited by examiner

PRODUCTION OF ALKYLAROMATIC COMPOUNDS

CROSS-REFERENCE TO RELATED APPLICATIONS

This application is a US national phase application of PCT Application Serial No. PCT/US2020/051086 having a filing date of Sep. 16, 2020, which claims priority to and the benefit of U.S. Provisional Application No. 62/916,427 having a filing date of Oct. 17, 2019 and European Patent Application No. 20154687.6 having a filing date of Jan. 30, 2020, the disclosures of all of which are incorporated herein by reference in their entireties.

FIELD

The present application relates to a process for producing alkylaromatic compounds, particularly ethylbenzene and cumene.

BACKGROUND

Ethylbenzene and cumene are valuable commodity chemicals which are used industrially for the production of styrene monomer and the coproduction of phenol and acetone, respectively. Ethylbenzene and cumene are typically produced by alkylating benzene with a $C_2$ or $C_3$ alkylating agent, such as ethylene or propylene, under liquid phase or mixed gas-liquid phase conditions in the presence of an acid catalyst, particularly a zeolite catalyst. In addition to the desired monoalkylated product, the process inevitably produces the dialkylated and trialkylated analogs as well as other heavy by-products. Thus, to maximize the yield of ethylbenzene and cumene, it is conventional to transalkylate the polyalkylated products with benzene to generate additional monoalkylated product. The product of the transalkylation reaction is then fed, together with the alkylkation reaction effluent, to one or more benzene columns, to recover unreacted benzene, then to one or more EB or cumene columns, to recover the desired monoalkylated product.

Current state-of-the-art transalkylation catalysts employ as the active materials metallosilicate zeolites having channels and/or surface pockets channel defined by 12-membered rings of tetrahedrally coordinated atoms. These zeolites can convert polyalkylbenzene molecules to ethylbenzene and cumene with high selectivity and activity. However, these catalysts require elevated temperatures, low flow rates of the substrate feed, and large catalyst beds to achieve sufficient conversion, all of which serve to increase process costs. Moreover, the problem is exacerbated by the fact that the trialkylated species are significantly less reactive than the dialkylated species so that, with existing catalysts, it is difficult to find a processing window where effective conversion of the trialkylated species is achieved without adversely affecting the selectivity of the conversion of the dialkylated species.

There is therefore significant interest in providing transalkylation catalysts which can operate at lower temperatures without sacrificing conversion activity and monalkylated benzene selectivity.

SUMMARY

It has now been found that zeolites having openings defined by 14-membered rings of tetrahedrally coordinated atoms are effective over a certain range of transalkylation conditions to catalyze the reaction of benzene with trialkylbenzenes, particularly triisopropylbenzene, to the monoalkylated species while retaining high selectivity of the conversion of the polyalkylated species to the desired monoalkylated species.

Thus, in one aspect, the present application resides in a process for producing a monoalkylated benzene, the process comprising: contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the catalyst composition comprises a metallosilicate zeolite comprising openings defined by 14-membered rings of tetrahedrally coordinated atoms and the transalkylation conditions include a temperature in the range of 160° C. to 220° C.

In another aspect, the present application resides in a process for producing a monoalkylated benzene, the process comprising:

(a) contacting a feedstream comprising benzene with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene;

(b) separating the alkylation effluent into a first fraction containing monoalkylated benzene and a second fraction containing dialkylated benzene and trialkylated benzene;

(c) contacting at least part of the second fraction with benzene in the presence of a transalkylation catalyst composition under transalkylation conditions effective to convert at least part of the dialkylated benzene and trialkylated benzene to monoalkylated benzene and produce a transalkylation effluent, wherein the transalkylation catalyst composition comprises a metallosilicate zeolite comprising openings defined by 14-membered rings of tetrahedrally coordinated atoms and the transalkylation conditions include a temperature in the range of 160° C. to 220° C.; and (d) recovering the monoalkylated benzene from the transalkylation effluent.

In a further aspect, the present application resides in a process for producing a monoalkylated benzene, the process comprising:

(a) contacting a feedstream comprising benzene with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene;

(b) separating the alkylation effluent into a first fraction containing monoalkylated benzene and a second fraction containing dialkylated benzene and trialkylated benzene;

(c) contacting at least part of the second fraction with benzene in the presence of a transalkylation catalyst composition under transalkylation conditions effective to convert at least part of the dialkylated benzene and trialkylated benzene to monoalkylated benzene and produce a transalkylation effluent, wherein the transalkylation catalyst composition comprises a metallosilicate zeolite having the structure of ITQ-27; and (d) recovering the monoalkylated benzene from the transalkylation effluent.

In yet a further aspect, the present application resides in a catalyst system for producing cumene, the catalyst system comprising:

(a) an alkylation catalyst composition comprising a zeolite selected from the group consisting of beta, faujasite, mordenite and a zeolite of the MCM-22 family for contacting a feedstream comprising benzene with propylene and/or isopropanol under alkylation conditions effective to convert at least part of the benzene in the feedstream to cumene and produce an alkylation effluent comprising cumene, di-isopropyl benzene and tri-isopropyl benzene, wherein the alkylation effluent is separated into a first fraction containing cumene and a second fraction containing di-isopropyl benzene and tri-isopropyl benzene; and (b) a transalkylation catalyst composition comprising a metallosilicate zeolite having the structure of ITQ-27 or UTD-1 for contacting at least part of the second fraction with benzene under transalkylation conditions including a temperature in the range of 160° C. to 220° C. effective to convert at least part of the di-isopropyl benzene and tri-isopropyl benzene to cumene, wherein the transalkylation conditions are such that the conversion of dialkylated benzene is at least 25% by weight.

DETAILED DESCRIPTION OF THE EMBODIMENTS

Figure 1:
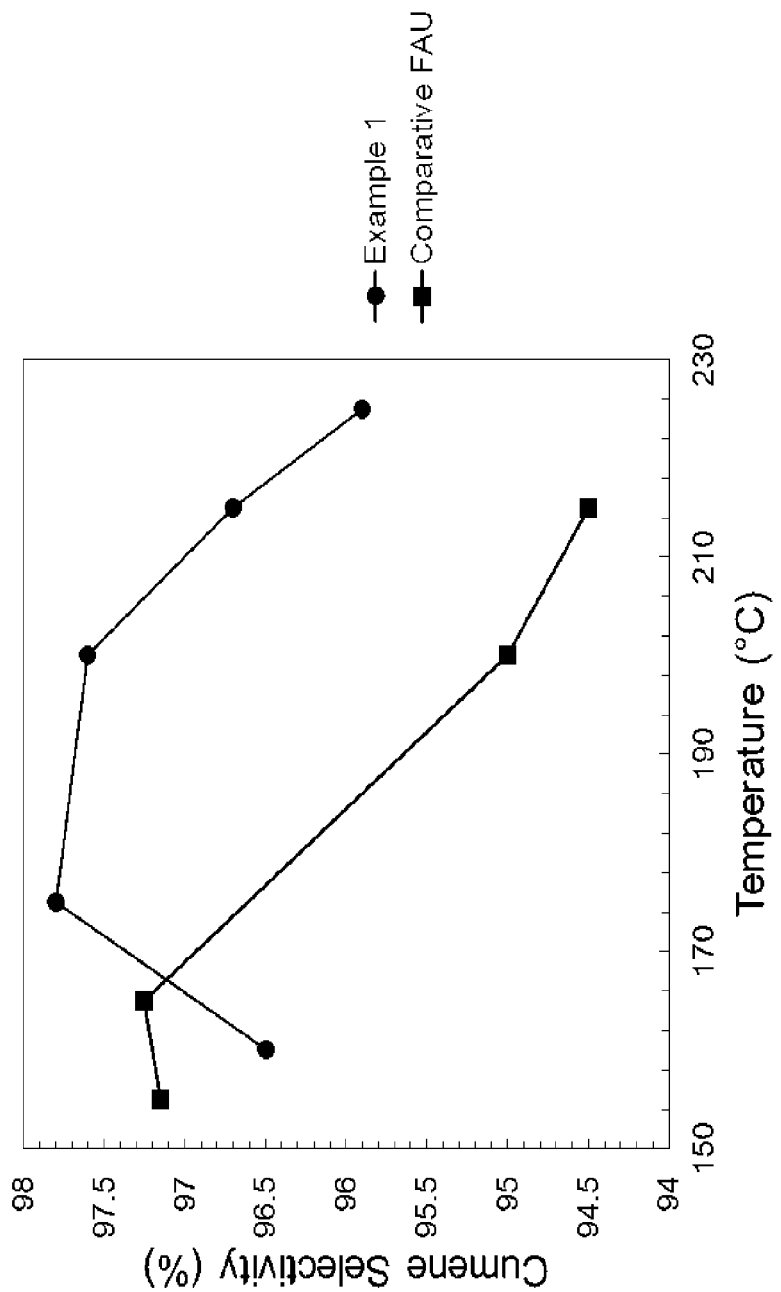
FIG. 1 is a graph comparing cumene selectivity with temperature for the UTD-1 catalyst of Example 1 with a commercially available faujasite catalyst in the transalkylation of an aromatic feed according to the process of Example 3.

Described herein is a process for producing monoalkylated benzenes, such as ethylbenzene and cumene, in which benzene is contacted with a mixture comprising dialkylated and trialkylated benzenes in the presence of a transalkylation catalyst composition under transalkylation conditions effective to convert at least part of the dialkylated and trialkylated benzene to monoalkylated benzene, wherein the transalkylation catalyst composition comprises a metallosilicate zeolite comprising openings defined by 14-membered rings of tetrahedrally coordinated atoms.

As used herein, the term "openings" includes channels or pores which connect the internal framework structure of the zeolite with its external surface as well as cavities that may be present on the external surface of the zeolite and/or internal cavities that link channels or pores penetrating the zeolite.

In one embodiment, the metallosilicate zeolite comprises UTD-1, which comprises one dimensional channels extending through the zeolite defined by a ring of 14 interconnected $SiO_4$ tetrahedral. The cross-sectional dimensions of the 14 ring channels are approximately 7.5 Å by 10 Å. The metal of the metallosilicate UTD-1 may be selected from the group consisting of aluminum, gallium, iron and indium oxide as well as from mixtures aluminum, boron, gallium, iron, indium, titanium and vanadium. In the present process, the metal is preferably aluminum, such that the zeolite has a silica to alumina molar ratio of 50 to 500, such as 50 to 200. Metallosilicate UTD-1 and its synthesis using bis(pentamethylcyclopentadienyl) cobalt (III) ions as directing agent are disclosed in U.S. Pat. No. 6,103,215, the entire contents of which are incorporated herein by reference.

In another embodiment, the metallosilicate zeolite comprises ITQ-27, which comprises a 2-dimensional channel system comprising 12-membered rings of tetrahedrally coordinated atoms interconnected by 14-membered ring openings. The 12-membered ring channels have cross-sectional dimensions of about 7.0 Å by about 6.2 Å. ITQ-27 may have the chemical formula $aX_2O_3:YO_2 \; nH_2O$, where X is any metal capable of tetrahedral coordination such as one or more of B, Ga, Al, Fe, Li, Be, P, Zn, Cr, Mg, Co, Ni, Be, Mn, As, In, Sn, Sb, Ti, and Zr, more preferably one or more trivalent metals capable of tetrahedral coordination, and even more preferably one or more of the elements B, Ga, Al, Fe, and Y is Si alone or in combination with any other tetravalent metal capable of tetrahedral coordination such as Ge and Ti and where a is from 0 to 0.005, and n is from 0 to 10. Generally, the ITQ-27 employed in the present process is an aluminosilicate. ITQ-27 and its synthesis using diphenyl-dimethyl-phosphonium ions as directing agent are disclosed in U.S. Pat. No. 7,527,782, the entire contents of which are incorporated herein by reference.

In a further embodiment, the catalyst employed in the present transalkylation process may comprise a mixture of UTD-1 and ITQ-27.

In addition to UTD-1 and/or ITQ-27, the catalyst employed in the present transalkylation process may comprise one of more additional molecular sieves, especially large pore molecular sieves having a Constraint Index less than 2. Suitable large pore molecular sieves include zeolite beta, zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite Beta is described in U.S. Pat. Nos. 3,308,069, and Re. No. 28,341. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Another class of molecular sieve materials which may be used in combination with UTD-1 and/or ITQ-27 in the present transalkylation catalyst is the group of mesoporous crystalline materials exemplified by the MCM-41 and MCM-48 materials. These mesoporous crystalline materials are described in U.S. Pat. Nos. 5,098,684; 5,102,643; and 5,198,203. MCM-41, which is described in U.S. Pat. No. 5,098,684, is characterized by a microstructure with a uniform, hexagonal arrangement of pores with diameters of at least about 1.3 nm: after calcination it exhibits an X-ray diffraction pattern with at least one d-spacing greater than about 1.8 nm and a hexagonal electron diffraction pattern that can be indexed with a d100 value greater than about 1.8 nm which corresponds to the d-spacing of the peak in the X-ray diffraction pattern. The preferred catalytic form of this material is the aluminosilicate although other metallosilicates may also be utilized. MCM-48 has a cubic structure and may be made by a similar preparative procedure Other suitable molecular sieves for use in the present transalkylation catalyst in addition to UTD-1 and/or ITQ-27 include molecular sieves of the MCM-22 family As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513) and mixtures thereof.

The above molecular sieves may be used as the transalkylation or alkylation catalyst without any binder or matrix, i.e., in so-called self-bound form. Alternatively, the molecular sieve(s) may be composited with another material which is resistant to the temperatures and other conditions employed in the alkylation reaction. Such binder materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. Preferred binder materials may be selected from the group consisting of alumina, clay, silica, and/or metal oxides. The relative proportions of molecular sieve and binder may vary widely, with the sieve content ranging from about 1 to about 90 weight % and more usually with the zeolite/binder weight ratio in the catalyst composition being from 20/80 to about 80/20.

Suitable conditions for the transalkylation of both polyethylbenzenes and polyisopropylbenzenes with benzene over the present zeolite beta catalyst include a temperature of 100° C. to 300° C., a pressure of 696 kPa-a to 5100 kPa-a, a weight hourly space velocity of 0.5 to 200 $hr^{-1}$ based on the weight of polyalkylated aromatic compounds and a benzene/polyalkylate weight ratio 0.5:1 to 20:1. Preferred conditions include a temperature of 160° C. to 220° C., a pressure of 696 kPa-a to 4137 kPa-a, a weight hourly space velocity of 0.5 to 100 $hr^{-1}$ based on the weight of polyalkylated aromatic compounds and benzene/polyalkylate weight ratio 1:1 to 10:1. In one preferred embodiment, where the transalkylation feed comprises diisopropylbenzene and triisopropylbenzene and the desired monalkylated product comprises cumene, the transalkylation conditions comprise a temperature in the range of 160 to 200° C. Typically, the transalkylation conditions are controlled such that the polyalkylated aromatic compounds and the benzene are at least partially or predominantly in the liquid phase.

Depending on the composition of the transalkylation feed and the transalkylation conditions employed, it is found that the UTD-1 and/or ITQ-27 catalyst employed herein is effective in converting at least 25% by weight, preferably at least 50%_by weight, of dialkylated benzene in the feed to the equivalent monalkylated product, typically with the weight ratio of the conversion of trialkylated benzene to the conversion of dialkylated benzene being at least 0.25, such as from 0.25 to 1.27.

Any mixture of dialkylated and trialkylated benzenes can be used in the present transalkylation process, although in most practical embodiments the polyalkylated benzene feedstock used herein will comprise part or all of the heavy fraction remaining after separation of a desired monalkylated product, especially ethylbenzene or cumene, from the reaction effluent of the alkylation of benzene with an alkylating agent, especially a $C_2$ or $C_3$ alkylating agent. In such a case, the polyalkylated benzene feedstock will typically contain from 40% by weight to 85% by weight of the dialkylated benzene and from 5% by weight to 60% by weight, or from 15% by weight to 60% by weight, of the trialkylated benzene.

Thus, in a further aspect, the present invention relates to a process for producing a monoalkylated benzene, in which a feedstream comprising benzene is initially contacted with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene. The alkylation effluent is then separated into a first fraction containing the monoalkylated benzene and a second fraction containing the dialkylated benzene and the trialkylated benzene. At least part of the second fraction is then contacted with additional benzene in the presence of the transalkylation catalyst composition as described above to convert at least part of the dialkylated benzene and trialkylated benzene to monoalkylated benzene and produce a transalkylation effluent, from which the monoalkylated benzene can be recovered.

The above process can find utility with a wide range of alkylating agents, but has particular advantage with $C_2$ and $C_3$ alkylating agents. Suitable alkylating agents are olefins and alcohols, which may be linear, branched or cyclic. In some embodiments, the alkylating agent is a $C_2$ alkylating agent, such as ethylene, or a $C_3$ alkylating agent, such as propylene and/or isopropanol. Preferably, the alkylating agent comprises propylene and/or isopropanol and the desired monoalkylated benzene product comprises cumene.

Suitable alkylation catalyst compositions comprises any or all of the molecular sieves discussed above in relation to the transalkylation catalyst, including zeolite UTD-1 and zeolite ITQ-27. In addition, the alkylation catalyst may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. Preferred alkylation catalysts comprise zeolite beta or a zeolite of the MCM-22 family. The above molecular sieves may be used as the alkylation catalyst without any binder or matrix or can be combined with any of the binder materials discussed above as suitable for use in the transalkylation catalyst.

The reaction conditions used to conduct the alkylation step will depend on the particular alkylating agent employed, but suitable conditions are well within the ambit of anyone of ordinary skill in the art. For example, alkylation of benzene with ethylene to produce ethylbenzene is typically conducted at a temperature about 120° C. to 300° C., preferably, a temperature of from about 150° C. to 260° C., a pressure of 500 to 8300 kPa-a, preferably, a pressure of 1500 to 4500 kPa-a, so that at least part of the reaction mixture is maintained in the liquid phase during the process. Generally, the molar ratio of benzene to ethylene is from about 1 to about 100, preferably from about 20 to about 80. In the case of alkylation of benzene with propylene to produce cumene, typical reaction conditions include a temperature of about 20° C. to about 350° C., for example about 50° C. to about 300° C., such as about 100° C. to about 280° C., and a pressure of about 100 kPa to about 20,000 kPa, for example about 500 kPa to about 10,000 kPa, so that at least part of the reaction mixture is maintained in the liquid phase during the process. Generally, the molar ratio of benzene to propylene is maintained within the range of about 1:1 to about 30:1, typically from 1.1:1 to 10:1.

In addition to the desired monoalkylated aromatic product, the effluent from the main alkylation reaction may contain significant quantities of unreacted benzene, together with smaller quantities of polyalkylated species, for example diisopropylbenzene (DIPB) and some triisopropylbenzene (TIPB) in a cumene process, and diethylbenzene (DEB) and some triethylbenzene (TEB) in an ethylbenzene process. The effluent from the main alkylation reaction is therefore fed to a separation system to allow recovery of the monoalkylated aromatic product and further processing of the by-products and impurities.

The separation system may include one or more benzene distillation columns, where unreacted benzene may be removed from the effluent as an overhead or side stream for recycle to the alkylation reaction and/or to the transalkylation reactor (as described above).

The bottoms from the benzene column(s) can then be fed to one or more monoalkylate distillation columns to recover the desired monoalkylated aromatic product. The bottoms from the monoalkylate column(s) contain the majority of the byproducts of the alkylation reaction heavier than the desired monoalkylate product. This bottoms stream may then be fed to one or more polyalkylate distillation columns to separate a polyalkylated aromatic product stream containing most of the dialkylated by-product and part of the trialkylated by-product for passage to the transalkylation reaction. The remainder of the trialkylated by-product and essentially all of the compounds heavier than the trialkylated by-product may be discharged at the bottoms of the polyalkylate column as residue.

The term "impurities" as used herein includes, but is not limited to, compounds having at least one of the following elements: nitrogen, halogens, oxygen, sulfur, arsenic, selenium, tellurium, phosphorus, and Group 1 through Group 12 metals.

In some embodiments, where the benzene feedstream to the alkylation and/or transalkylation reaction comprises impurities, the process further comprises: contacting the benzene feedstream with an absorbent under conditions effective to remove at least part of the impurities. The adsorbent may have catalytic activity and may comprise a molecular sieve, such as any of the molecular sieves described above, and a small quantity of alkylating agent may be simultaneously fed to the adsorbent to react with the benzene feed and thereby act as a marker for poison capacity of the adsorbent.

The invention will now be more particularly described with reference to the following non-limiting Examples and the accompanying drawings.

Example 1: Preparation of 80% UTD-1/20% Versal-300 Catalyst

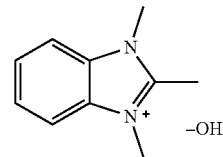

In a tarred vessel, 8.96 g of deionized water, 36 g of 10.5 wt % 1,2,3-trimethylbenzimidazolium hydroxide (see above), 13.12 g of colloidal silica (Ludox® LS, 30 wt % solution), 0.416 g of MS-25 an amorphous silica/alumina, and 0.0125 g of seed crystals was heated at 160° C., for 10 days. The product was isolated via filtration and rinsed with 400 mL of deionized water followed by 50 mL of acetone. The product was dried overnight in a 100° C. oven and yielded 4.4 g of UTD-1. The sample was then calcined by heating under nitrogen to 600° C. for 2 h. A mixture of 80 wt % UTD-1 as described above and 20 wt % of an alumina binder supplied by Honeywell UOP under the tradename Versal-300 was extruded into a 1/20" quadrolobe shape. The product was predried in flowing N2 at 900° F. (482° C.), exchanged with ammonium nitrate, and calcined at 1000° F. (538° C.) under air.

Example 2: Preparation of 65% ITQ-27/35% Versal-300 Catalyst

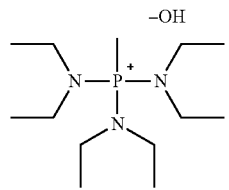 [SMILES: CCN(CC)[P+](C)(N(CC)CC)N(CC)CC]

To a tarred vessel containing 17.3 g of tris(diethylamino) (methyl)phosphonium hydroxide (see above), 0.23 g of aluminum isopropoxide was added with stirring until dissolved. To this solution was added 5.08 g of tetramethyl orthosilicate and the reaction mixture was allowed to hydrolyze for 20 min. Then, 0.67 g of 50 wt % HF was added dropwise, the reaction was mixed thoroughly, and the volume reduced via evaporation overnight. After reconstitution, 0.04 g of seed crystals were added and the reaction was heated at 150° C. for 6 days. The product was isolated via filtration and rinsed with 400 mL of deionized water followed by 50 mL of acetone. The product was dried overnight in a 100° C. oven and yielded 2.45 g of ITQ-27. A mixture of 65 wt % ITQ-27 as described above and 35 wt % of an alumina binder supplied by Honeywell UOP under the tradename Versal-300 was extruded into a 1/16" cylinder shape. The product was predried in flowing $N_2$ at 900° F. (482° C.), exchanged with ammonium nitrate, and calcined at 1000° F. (538° C.) under air.

Example 3

A first series of tests were run in which a mixture comprising 74 wt % benzene, 20 wt % DIPB and 6 wt % TIPB was contacted separately with the catalyst of Example 1 and with a commercially available sample of faujasite supplied by Zeolyst and having a silica to alumina molar ratio of 12. A second series of tests were run in which a mixture comprising 60 wt % benzene, 30 wt % DIPB and 10 wt % TIPB was contacted separately with the catalyst of Example 2 and with the same faujasite catalyst as used in the first series of tests. Each test series was conducted at a pressure of 2070 kPa-a and at various temperatures between 150 and 225° C. and the selectivity of the conversion of the DIPB and TIPB to cumene was measured for each run. The results are shown in FIGS. 1 to 4.

Figure 2:
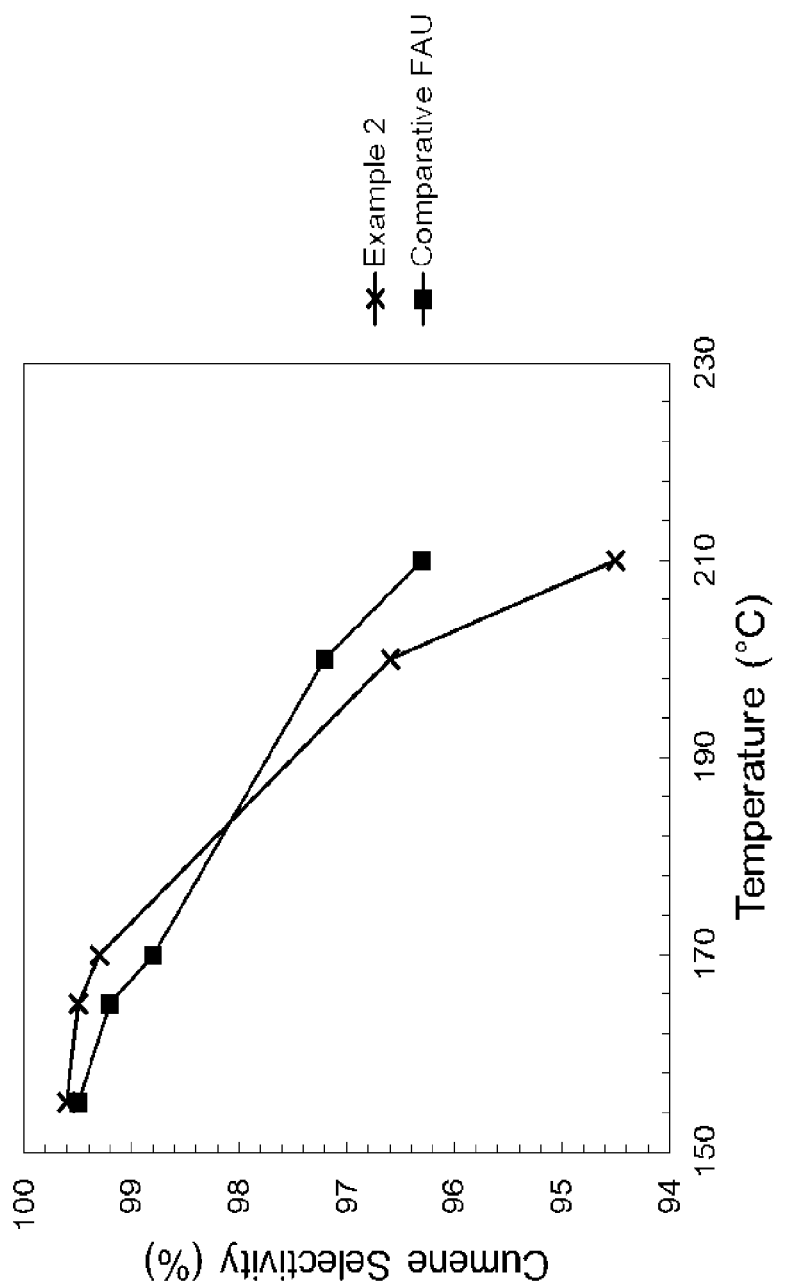
FIG. 2 is a graph comparing cumene selectivity with temperature for the ITQ-27 catalyst of Example 2 with a commercially available faujasite catalyst in the transalkylation of an aromatic feed according to the process of Example 3.
Figure 3:
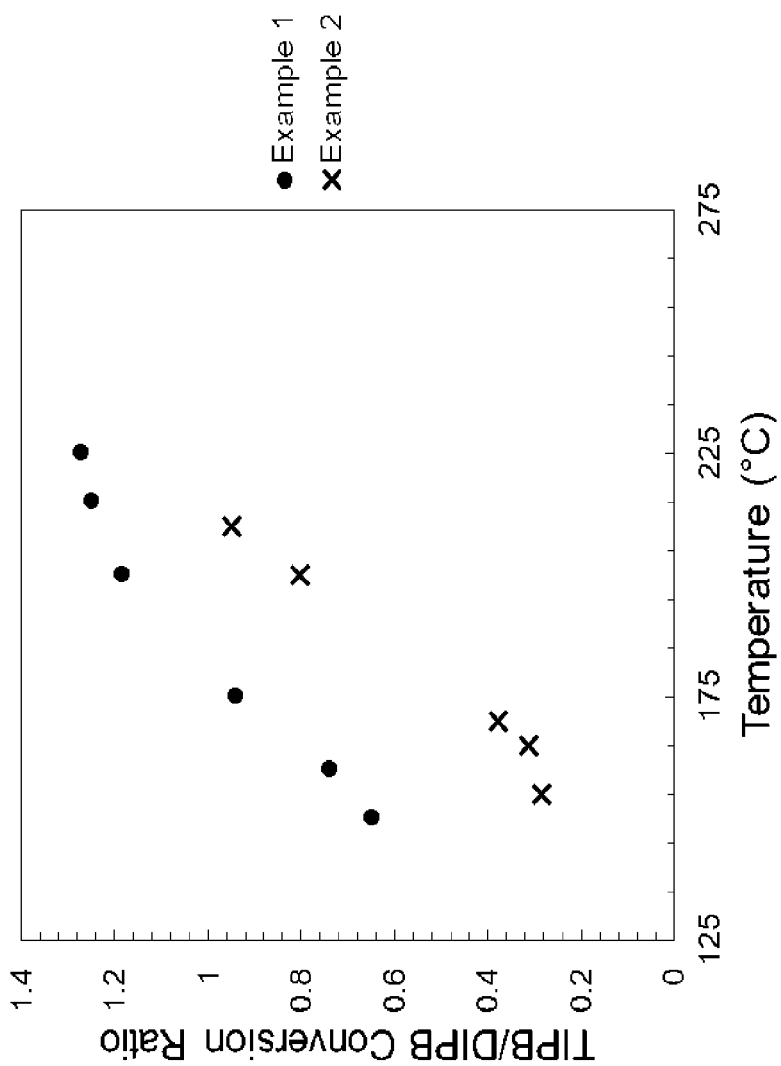
FIG. 3 is a graph plotting TIPB/DIPB conversion ratio against temperature for the catalysts of Examples 1 and 2 when tested according to the process of Example 3.
Figure 4:
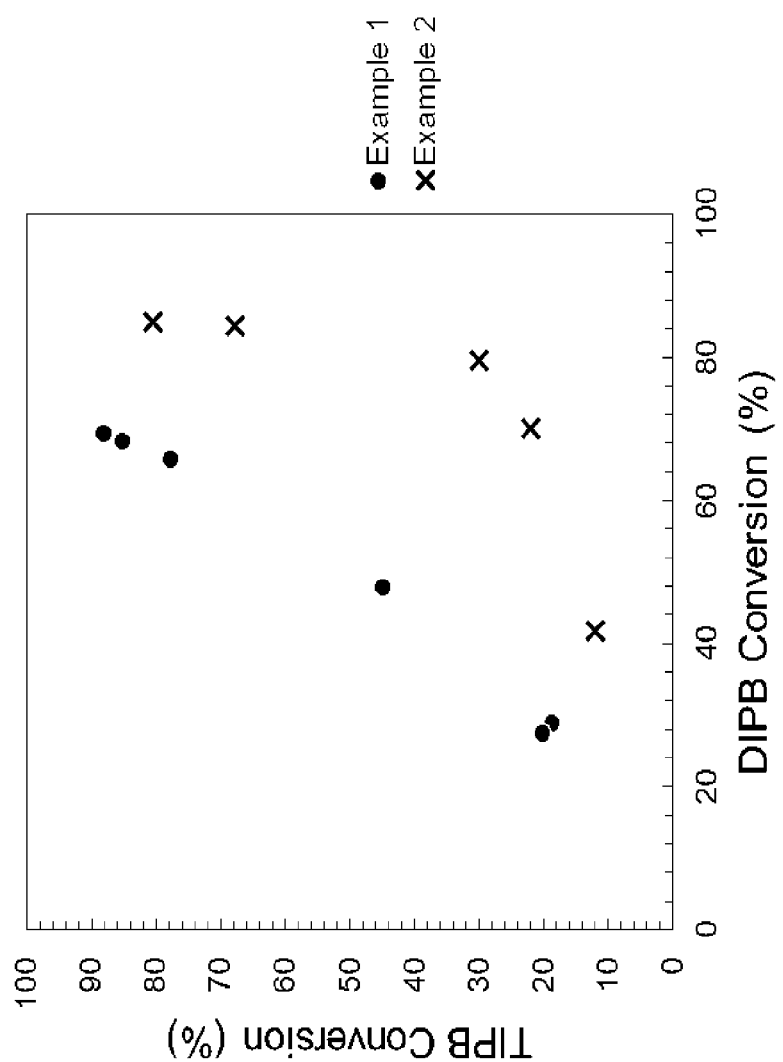
FIG. 4 is a graph plotting TIPB conversion against DIPB conversion for the catalysts of Examples 1 and 2 when tested according to the process of Example 3.

It will be seen from FIG. 1 that the UTD-1 catalyst of Example 1 consistently exhibited a cumene selectivity of 96.5 to 97.8% by weight over a temperature range of 160 to 220° C., whereas the cumene selectivity of the faujasite catalyst fell continuously from around 97% by weight at 160° C. to about 94% by weight at 210° C. FIG. 2 shows that, although the differences in performance between the ITQ-27 catalyst and the faujasite catalyst were small, both exhibited cumene selectivity of over 99% by weight at 160° and over 97% by weight at 200° C. FIG. 3 shows that weight ratio of the conversion of trialkylated benzene to the conversion of dialkylated benzene was at least 0.25 with the UTD-1 catalyst of Example 1 and was at least 0.6 with the ITQ-27 catalyst of Example 2. FIG. 4 shows that the conversion of dialkylated benzene was at least 25 wt % for both the catalysts of Examples 1 and 2.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing a monoalkylated benzene, the process comprising: contacting benzene with a mixture comprising dialkylated and trialkylated benzenes in the presence of a transalkylation catalyst composition under transalkylation conditions effective to convert at least part of the dialkylated and trialkylated benzenes to monoalkylated benzene, wherein the catalyst composition comprises a metallosilicate zeolite comprising openings defined by 14-membered rings of tetrahedrally coordinated atoms having the structure of ITQ-27, and the transalkylation conditions include a temperature in the range of 160 ° C. to 220 ° C., wherein the dialkylated benzenes comprise diisopropylbenzene, diethylbenzene, or both, and wherein the trialkylated benzenes comprise triisopropylbenzene, triethylbenzene, or both.

2. The process of claim 1, wherein the 14-membered ring openings define pores communicating with the external surface of the metallosilicate zeolite.

3. A process for producing a monoalkylated benzene comprising the step of contacting benzene with a mixture comprising dialkyllated and trialkylated benzenes in the presence of a transalkylation catalyst composition under transalkylation conditions effective to convert at least part of the dialkylated and trialkylated benzenes to monoalkylated benzene, wherein the catalyst composition comprises a metallosilicate zeolite having the structure of ITQ-27.

4. The process of claim 3, wherein the transalkylation conditions include a temperature in the range of 160 ° C. to 220 ° C.

5. The process of claim 1, wherein the transalkylation conditions are such that the weight ratio of the conversion of trialkylated benzene to the conversion of dialkylated benzene is at least 0.28.

6. The process of claim 1, wherein the transalkylation conditions are such that the weight ratio of the conversion of trialkylated benzene to the conversion of dialkylated benzene is in the range of 0.25 to 1.27.

7. The process of claim 1, wherein the transalkylation conditions are such that the conversion of dialkylated benzene is at least 25% by weight.

8. The process of claim 1, wherein the monoal.kylated benzene comprises cumene.

9. The process of claim 1, wherein the transalkylation catalyst composition further comprises one or more binders selected from the group consisting of alumina, clay, silica, and metal oxides, wherein the zeolite/binder weight ratio in the catalyst composition is from 20/80 to about 80/20.

10. A process for producing a monoalkylated benzene, the process comprising:
(a) contacting a feedstream comprising benzene with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene;
(b) separating the alkylation effluent into a first fraction containing monoalkylated benzene and a second fraction containing dialkylated benzene and. trialkylated benzene;
(c) contacting at least part of the second fraction with benzene in the presence of a transalkylation catalyst composition under transalkylation conditions effective to convert at least part of the dialkylated benzene and trialkylated benzene to monoalkylated benzene and produce a transalkylation effluent, wherein the transalkylation catalyst composition comprises a metallosilicate zeolite comprising openings defined by 14-membered rings of tetrahedrally coordinated atoms having the structure of ITO-27 and the transalkylation conditions include a temperature in the range of 160 °C to 220 ° C. ; and
(d) recovering the monoalkylated benzene from the transalkylation effluent.

11. The process of claim 10, wherein the 14-membered ring openings define pores communicating with the external surface of the metallosilicate zeolite.

12. A process for producing a monoalkylated benzene, the process comprising:
(a) contacting a feedstream comprising benzene with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and id alkylated benzene;
(b) separating the alkylation effluent into a first fraction containing monoalkylated benzene and a second fraction containing di alkylated benzene and trialkylated benzene;
(c) contacting at least part of the second fraction with benzene in the presence of a transalkylation catalyst composition under transalkylation conditions effective to convert at least part of the dialkylated benzene and trialkylated benzene to monoalkylated benzene and produce a transalkylation effluent, wherein the transalkylation catalyst composition comprises a metallosilicate zeolite having the structure of ITQ-27; and
(d) recovering the monoalkylated benzene from the transalkylation effluent.

13. The process of claim 12, wherein the transalkylation conditions include a temperature in the range of 160 ° C. to 220 ° C.

14. The process of claim 10, wherein the alkylation catalyst composition comprises a zeolite selected from the group consisting of beta, faujasite, mordenite and a zeolite of the MCM-22 family.

15. The process of claim 10, wherein the transalkylation conditions are such that the weight ratio of the conversion of trialkylated benzene to the conversion of dialkylated benzene is at least 0.25.

16. The process of claim 10, wherein the transalkylation conditions are such that the weight ratio of the conversion of trialkylated benzene to the conversion of dial kylated benzene is in the range of 0.25 to 1.27.

17. The process of claim 10, wherein the transalkylation conditions are such that the conversion of dialkylated benzene is at least 25% by weight.

18. The process of claim 10, wherein the transalkylation catalyst composition further comprises one or more binders selected from the group consisting of alumina, clay, silica, and metal oxides, wherein the zeolite/binder weight ratio in the catalyst composition is from 20/80 to about 80/20.

19. The process of claim 10, wherein the alkylation effluent further comprises unreacted benzene and the process further comprises:
(e) separating the unreacted benzene from the alkylation effluent and recycling at least part of the unreacted benzene to the contacting (a), the contacting (c), or both.

20. The process of claim 10, wherein the transalkylation effluent further comprises unreacted benzene and the process further comprises:
(f) separating the unreacted benzene from the transalkylation effluent and recycling at least part of the unreacted benzene to the contacting (a), the contacting (c), or both.

21. The process of claim 10, wherein the feedstream further comprises impurities and the process further comprises:
(g) contacting the feedstream with an absorbent under conditions effective to remove at least part of the impurities, wherein the impurities comprise compounds having at least one of the following elements: nitrogen, halogens, oxygen, sulfur, arsenic, selenium, tellurium, phosphorus, and Group 1 through Group 12 metals.

* * * * *